(12) United States Patent  (10) Patent No.: US 8,455,496 B2
Pfefferkorn et al.  (45) Date of Patent: Jun. 4, 2013

(54) BENZOFURANYL DERIVATIVES

(75) Inventors: Jeffrey Allen Pfefferkorn, Mystic, CT (US); Anthony Lai Ling, San Diego, CA (US)

(73) Assignee: Pfizer Inc., New York, NY (US)

( * ) Notice: Subject to any disclaimer, the term of this patent is extended or adjusted under 35 U.S.C. 154(b) by 371 days.

(21) Appl. No.: 12/720,724

(22) Filed: Mar. 10, 2010

(65) Prior Publication Data

US 2010/0234285 A1   Sep. 16, 2010

Related U.S. Application Data

(60) Provisional application No. 61/159,099, filed on Mar. 11, 2009.

(51) Int. Cl.
*A61K 31/497* (2006.01)

(52) U.S. Cl.
USPC ........ 514/252.1; 514/183; 514/247; 514/256; 514/269; 514/449; 514/461; 514/468

(58) Field of Classification Search
None
See application file for complete search history.

(56) References Cited

U.S. PATENT DOCUMENTS

| | | | |
|---|---|---|---|
| 4,404,214 A | 9/1983 | Takeda et al. | |
| 5,972,936 A | 10/1999 | Dyke et al. | 514/233.5 |
| 6,066,657 A | 5/2000 | Dyke et al. | 514/337 |
| 6,117,874 A | 9/2000 | Dombroski et al. | 514/253.07 |
| 6,121,274 A | 9/2000 | Ulrich et al. | 514/278 |
| 6,133,286 A | 10/2000 | Dombroski et al. | 514/312 |
| 6,211,203 B1 | 4/2001 | Amschier | 514/337 |
| 7,842,713 B2 | 11/2010 | Bai et al. | 514/406 |
| 8,071,606 B2 | 12/2011 | Benbow et al. | |
| 8,119,624 B2 | 2/2012 | Bai et al. | |
| 2003/0139402 A1 | 7/2003 | Konradi et al. | |
| 2004/0138286 A1 | 7/2004 | Imazaki et al. | |
| 2004/0147512 A1 | 7/2004 | Konradi et al. | |
| 2004/0214868 A1 | 10/2004 | Hayter et al. | |
| 2005/0026969 A1 | 2/2005 | Cheng et al. | 514/363 |
| 2005/0113420 A1 | 5/2005 | Nan et al. | |
| 2006/0058353 A1 | 3/2006 | Mckerrecher et al. | 514/337 |
| 2006/0142269 A1 | 6/2006 | Dykes | 514/218 |
| 2006/0148888 A1 | 7/2006 | Krauss et al. | 514/456 |
| 2006/0167053 A1 | 7/2006 | Iino et al. | |
| 2006/0205751 A1 | 9/2006 | Lee et al. | 514/281 |
| 2006/0258701 A1 | 11/2006 | Mitsuya et al. | |
| 2006/0287291 A1 | 12/2006 | Johansson et al. | 514/210.19 |
| 2007/0213349 A1 | 9/2007 | Cheruvallath et al. | |
| 2011/0039821 A1 | 2/2011 | Bai et al. | 514/210.18 |

FOREIGN PATENT DOCUMENTS

| | | |
|---|---|---|
| EP | 0606489 | 7/1993 |
| EP | 1433778 | 6/2004 |
| EP | 1532980 | 5/2005 |
| JP | 2006177436 | 7/2006 |
| WO | 9304580 | 3/1993 |
| WO | 9610016 | 9/1996 |
| WO | 9728133 | 8/1997 |
| WO | 0066557 | 11/2000 |
| WO | 0220463 | 3/2002 |
| WO | 0240448 | 5/2002 |
| WO | 0246173 | 6/2002 |
| WO | 02051836 | 7/2002 |
| WO | 03/035621 | 5/2003 |
| WO | 03068230 | 8/2003 |
| WO | 03092670 | 11/2003 |
| WO | 03106427 | 12/2003 |
| WO | WO 2004 046139 | 6/2004 |
| WO | WO2004046139 | * 6/2004 |
| WO | 2004072066 | 8/2004 |
| WO | 2004/074262 | 9/2004 |
| WO | 2005018557 | 3/2005 |
| WO | 2005095418 | 10/2005 |
| WO | 2006015159 | 2/2006 |
| WO | 2006028833 | 3/2006 |
| WO | WO 2006 030031 | 3/2006 |
| WO | 2006098683 | 9/2006 |
| WO | WO 2006 106326 | 10/2006 |

(Continued)

OTHER PUBLICATIONS

Fyfe, et al., "Glucokinase activator PSN-GK1 displays enhanced antihyperglycaemic and insulinotropic actions", Diabetologia, vol. 50, pp. 1277-1287 (2007).
Jordan, "Tamoxifen: A Most Unlikely Pioneering Medicine", Nature Reviews: Drug Discovery, vol. 2, pp. 205-213 (2003).
Hackam, et al., "Translation of Research Evidence From Animals to Humans", JAMA, vol. 296(14), pp. 1731-1732 (2006).

(Continued)

*Primary Examiner* — Cecilia J Tsang
*Assistant Examiner* — Fred Reynolds
(74) *Attorney, Agent, or Firm* — James T. Wasicak

(57) ABSTRACT

The present invention provides compounds of Formula (I)

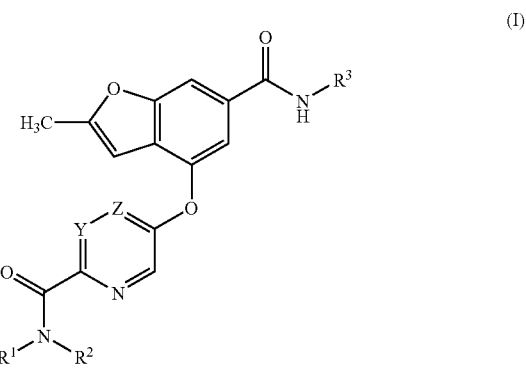

that act as glucokinase activators; pharmaceutical compositions thereof; and methods of treating diseases, disorders, or conditions mediated by glucokinase.

6 Claims, No Drawings

FOREIGN PATENT DOCUMENTS

| WO | 2007/022380 | 2/2007 |
| WO | 2007026761 | 3/2007 |
| WO | 2007/043638 | 4/2007 |
| WO | WO 2007 043638 | 4/2007 |
| WO | 2007058580 | 5/2007 |
| WO | WO 2007 117995 | 10/2007 |
| WO | WO 2007 122482 | 11/2007 |
| WO | WO2007122482 | * 11/2007 |
| WO | WO 2008 079787 | 12/2007 |
| WO | 2008120754 | 10/2008 |
| WO | 2008149382 | 12/2008 |

OTHER PUBLICATIONS

Krause, et al., "N-Terminal pyrazinones: a new class of peptide-bound advanced glycation and end-products", Amino Acids, vol. 27(1), pp. 9-18 (2004).

Janusz et al., Journal of Medicinal Chemistry, vol. 41, p. 3515-3529, 1998.

Sarabu et al., Expert Opinion on Therapeutic Patents, vol. 18, No. 7, pp. 759-768, 2008.

Moller, Nature, vol. 414, pp. 821-827, 2001.

* cited by examiner

BENZOFURANYL DERIVATIVES

This application claims the benefit under 35 USC 119(e) from U.S. Provisional Patent Application No. 61/159,099 filed Mar. 11, 2009.

FIELD OF THE INVENTION

The present invention relates to substituted benzofuranyl derivatives, as well as pharmaceutical compositions and uses thereof as glucokinase activators.

BACKGROUND

Diabetes is a major public health concern because of its increasing prevalence and associated health risks. The disease is characterized by metabolic defects in the production and utilization of carbohydrates which result in the failure to maintain appropriate blood glucose levels. Two major forms of diabetes are recognized. Type I diabetes, or insulin-dependent diabetes mellitus (IDDM), is the result of an absolute deficiency of insulin. Type II diabetes, or non-insulin dependent diabetes mellitus (NIDDM), often occurs with normal, or even elevated levels of insulin and appears to be the result of the inability of tissues and cells to respond appropriately to insulin. Aggressive control of NIDDM with medication is essential; otherwise it can progress into IDDM.

As blood glucose increases, it is transported into pancreatic beta cells via a glucose transporter. Intracellular mammalian glucokinase (GK) senses the rise in glucose and activates cellular glycolysis, i.e. the conversion of glucose to glucose-6-phosphate, and subsequent insulin release. Glucokinase is found principally in pancreatic β-cells and liver parenchymal cells. Because transfer of glucose from the blood into muscle and fatty tissue is insulin dependent, diabetics lack the ability to utilize glucose adequately which leads to undesired accumulation of blood glucose (hyperglycemia). Chronic hyperglycemia leads to decreases in insulin secretion and contributes to increased insulin resistance. Glucokinase also acts as a sensor in hepatic parenchymal cells which induces glycogen synthesis, thus preventing the release of glucose into the blood. The GK processes are thus critical for the maintenance of whole body glucose homeostasis.

It is expected that an agent that activates cellular GK will facilitate glucose-dependent secretion from pancreatic beta cells, correct postprandial hyperglycemia, increase hepatic glucose utilization and potentially inhibit hepatic glucose release. Consequently, a GK activator may provide therapeutic treatment for NIDDM and associated complications, inter alia, hyperglycemia, dyslipidemia, insulin resistance syndrome, hyperinsulinemia, hypertension, and obesity.

Several drugs in five major categories, each acting by different mechanisms, are available for treating hyperglycemia and subsequently, NIDDM (Moller, D. E., "New drug targets for Type 2 diabetes and the metabolic syndrome" Nature 414; 821-827, (2001)): (A) Insulin secretogogues, including sulphonyl-ureas (e.g., glipizide, glimepiride, glyburide) and meglitinides (e.g., nateglidine and repaglinide) enhance secretion of insulin by acting on the pancreatic beta-cells. While this therapy can decrease blood glucose level, it has limited efficacy and tolerability, causes weight gain and often induces hypoglycemia. (B) Biguanides (e.g., metformin) are thought to act primarily by decreasing hepatic glucose production. Biguanides often cause gastrointestinal disturbances and lactic acidosis, further limiting their use. (C) Inhibitors of alpha-glucosidase (e.g., acarbose) decrease intestinal glucose absorption. These agents often cause gastrointestinal disturbances. (D) Thiazolidinediones (e.g., pioglitazone, rosiglitazone) act on a specific receptor (peroxisome proliferator-activated receptor-gamma) in the liver, muscle and fat tissues. They regulate lipid metabolism subsequently enhancing the response of these tissues to the actions of insulin. Frequent use of these drugs may lead to weight gain and may induce edema and anemia. (E) Insulin is used in more severe cases, either alone or in combination with the above agents.

Ideally, an effective new treatment for NIDDM would meet the following criteria: (a) it would not have significant side effects including induction of hypoglycemia; (b) it would not cause weight gain; (c) it would at least partially replace insulin by acting via mechanism(s) that are independent from the actions of insulin; (d) it would desirably be metabolically stable to allow less frequent usage; and (e) it would be usable in combination with tolerable amounts of any of the categories of drugs listed herein.

Substituted heteroaryls, particularly pyridones, have been implicated in mediating GK and may play a significant role in the treatment of NIDDM. For example, U.S. Patent publication No. 2006/0058353 and PCT publication No's. WO2007/043638, WO2007/043638, and WO2007/117995 recite certain heterocyclic derivatives with utility for the treatment of diabetes. Although investigations are on-going, there still exists a need for a more effective and safe therapeutic treatment for diabetes, particularly NIDDM.

SUMMARY

The present invention provides compounds of Formula (I) that act as glucokinase mediators, in particular, glucokinase activators; therefore, may be used in the treatment of diseases mediated by such activation (e.g., diseases related to Type 2 diabetes, and diabetes-related and obesity-related co-morbidities),

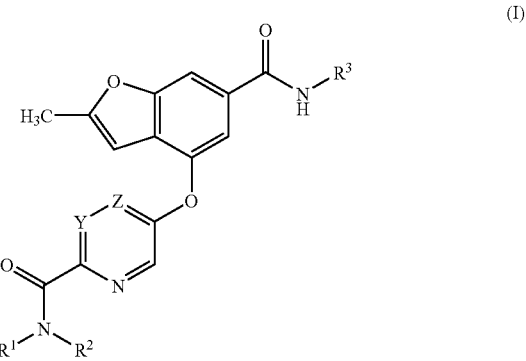

(I)

wherein, Y is N and Z is C, or Y is C and Z is N; $R^1$ and $R^2$ are each independently methyl or ethyl; and $R^3$ is 5-methylpyrazin-2-yl, 5-methoxypyrazin-2-yl, or 1-methyl-1H-pyrazol-3-yl; or a pharmaceutically acceptable salt thereof.

In one preferred embodiment, Y is N and Z is C.

In another preferred embodiment, Y is C and Z is N.

A preferred compound of Formula (I) is a compound where $R^1$ and $R^2$ are both methyl; and $R^3$ is 5-methylpyrazin-2-yl; or a pharmaceutically acceptable salt thereof.

A preferred compound is N,N-dimethyl-5-(2-methyl-6-((5-methylpyrazin-2-yl)carbamoyl-benzofuran-4-yloxy) pyrazine-2-carboxamide.

Another preferred compound is N,N-dimethyl-5-(2-methyl-6-((5-methylpyrazin-2-yl)carbamoyl)-benzofuran-4-yloxy)pyrimidine-2-carboxamide.

Another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include anti-obesity agents and/or anti-diabetic agents (described herein below).

In yet another aspect of the present invention is a method for treating a disease, condition, or disorder mediated by glucokinase, in particular, activation of said enzyme, in a mammal that includes the step of administering to a mammal, preferably a human, in need of such treatment a therapeutically effective amount of a compound of the present invention, or a pharmaceutical composition thereof.

Diseases, disorders, or conditions mediated by glucokinase activators include Type II diabetes, hyperglycemia, metabolic syndrome, impaired glucose tolerance, glucosuria, cataracts, diabetic neuropathy, diabetic nephropathy, diabetic retinopathy, obesity, dyslididemia, hypertension, hyperinsulinemia, and insulin resistance syndrome. Preferred diseases, disorders, or conditions include Type II diabetes, hyperglycemia, impaired glucose tolerance, obesity, and insulin resistance syndrome. More preferred are Type II diabetes, hyperglycemia, and obesity. Most preferred is Type II diabetes.

In yet another aspect of the present invention is a method of reducing the level of blood glucose in a mammal, preferably a human, which includes the step of administering to a mammal in need of such treatment a therapeutically effective amount of a compound of the present invention, or a pharmaceutical composition thereof.

Compounds of the present invention may be administered in combination with other pharmaceutical agents (in particular, anti-obesity and anti-diabetic agents described herein below). The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

DEFINITIONS

As used herein, the term "alkyl" refers to a hydrocarbon radical of the general formula $C_nH_{2n+1}$. The alkane radical may be straight or branched. For example, the term "($C_1$-$C_6$) alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, alkylsulfonyl, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, 1,1-difluoroethyl and the like).

The term "cycloalkyl" refers to nonaromatic rings that are fully hydrogenated and may exist as a single ring, bicyclic ring or a spiral ring. Unless specified otherwise, the carbocyclic ring is generally a 3- to 8-membered ring. For example, cycloalkyl include groups such as cyclopropyl, cyclobutyl, cyclopentyl, cyclohexyl, cyclohexenyl, norbornyl(bicyclo[2.2.1]heptyl), bicyclo[2.2.2]octyl, and the like.

The term "heterocycle" refers to nonaromatic rings that are fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Heterocyclic rings include groups such as epoxy, aziridinyl, tetrahydrofuranyl, pyrrolidinyl, N-methylpyrrolidinyl, piperidinyl, piperazinyl, pyrazolidinyl, 4H-pyranyl, morpholino, thiomorpholino, tetrahydrothienyl, tetrahydrothienyl 1,1-dioxide, and the like.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated" or "modulating", or "modulate(s)", as used herein, unless otherwise indicated, refers to the activation of the activating the glucokinase enzyme with compounds of the present invention.

The terms "mediated" or "mediating" or "mediate(s)", as used herein, unless otherwise indicated, refers to the treatment or prevention the particular disease, condition, or disorder, (ii) attenuation, amelioration, or elimination of one or more symptoms of the particular disease, condition, or disorder, or (iii) prevention or delay of the onset of one or more symptoms of the particular disease, condition, or disorder described herein, by activating the glucokinase enzyme via glucose binding enhancement, alleviating the inhibition of glucokinase regulatory protein, a key regulator of glucokinase activity in the liver, and/or by increasing the catalytic rate of the glucokinase enzyme (e.g., change Vmax).

The term "compounds of the present invention" (unless specifically identified otherwise) refer to compounds of Formula (I) and any pharmaceutically acceptable salts of the compounds, as well as, all stereoisomers (including diastereoisomers and enantiomers), tautomers, conformational isomers, and isotopically labeled compounds. Hydrates and solvates of the compounds of the present invention are considered compositions of the present invention, wherein the compound is in association with water or solvent, respectively.

DETAILED DESCRIPTION

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, New York (1967-1999 ed.), or Beilsteins *Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Similarly, a "hydroxy-protecting group" refers to a substituent of a hydroxy group that blocks or protects the hydroxy functionality. Suitable hydroxyl-protecting groups (O-Pg) include for example, allyl, acetyl, silyl, benzyl, para-methoxybenzyl, trityl, and the like. The need for such protection is readily determined by one skilled in the art. For a general description of protecting groups and their use, see T. W. Greene, *Protective Groups in Organic Synthesis*, John Wiley & Sons, New York, 1991.

Scheme I outlines the general procedures one could use to provide compounds of the present invention having Formula (I).

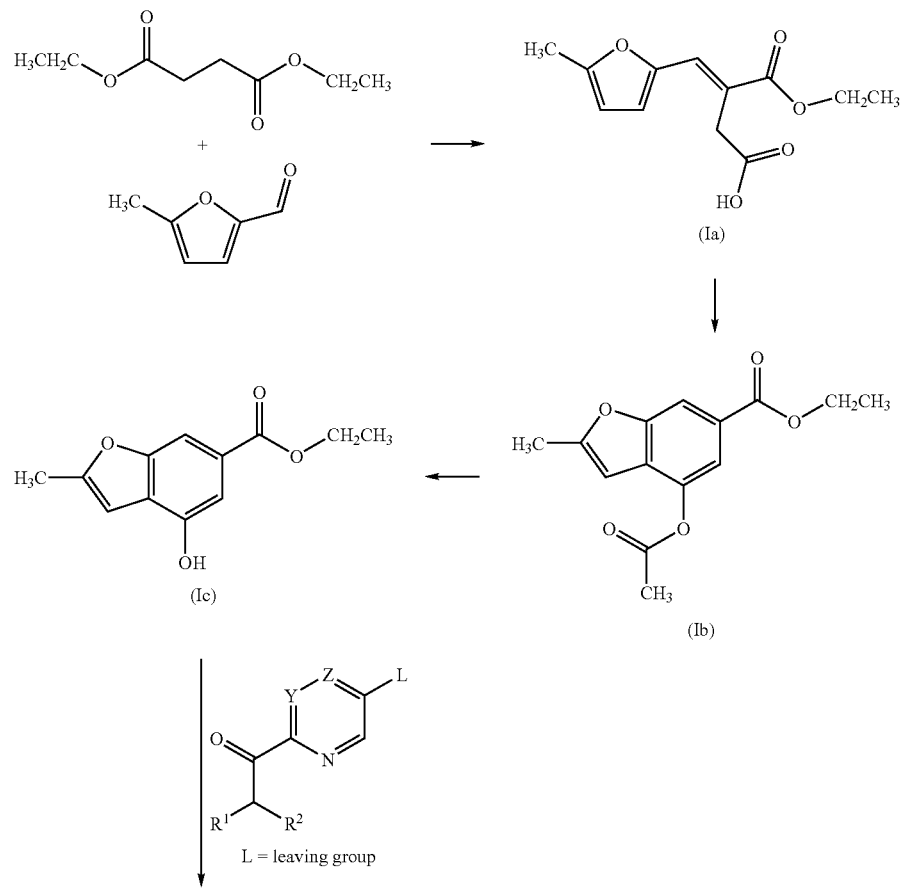

L = leaving group

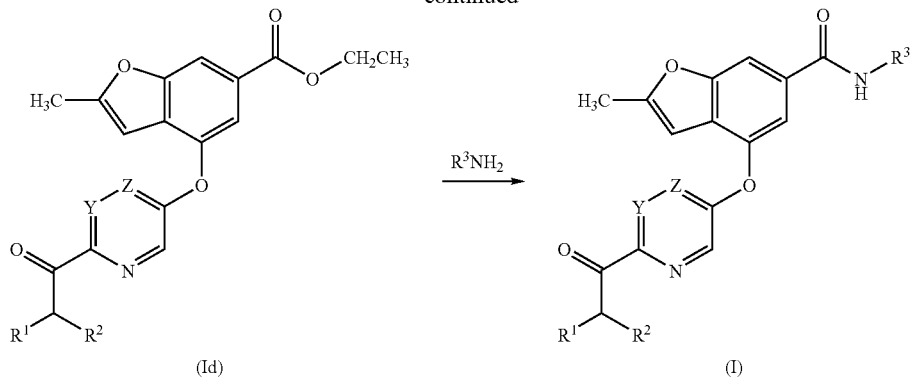

Diethyl succinate and 5-methyl-2-furaldehyde can be condensed to form intermediate (Ia) using conventional aldo condensation reaction conditions. For example, the two starting materials can be treated with a strong base and heat (e.g., sodium ethoxide in refluxing ethanol) followed by acidification. The benzofuran ring in intermediate (1b) may be formed by treatment of intermediate (1a) with acetic anhydride and sodium acetate at about room temperature followed by heating to reflux. The acetate group may then be removed to provide the hydroxyl intermediate (1c) which then allows the addition of the desired pyrazinylamide or pyrimidylamide moiety via the free hydroxyl group to form intermediate (1d). Intermediate (1d) can then be reacted with the desired amine ($R^3NH_2$) to form a compound of formula (I) via standard amidation reaction conditions well known to those of skill in the art. The examples below provide a more detailed description of the reaction conditions described above.

The compounds of the present invention may be isolated and used per se, or when possible, in the form of its pharmaceutically acceptable salt. The term "salts" refers to inorganic and organic salts of a compound of the present invention. These salts can be prepared in situ during the final isolation and purification of a compound, or by separately reacting the compound with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1-19 (1977).

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Certain compounds of the present invention may exist in different stable conformational forms which may be separable. Torsional asymmetry due to restricted rotation about an asymmetric single bond, for example, because of steric hindrance or ring strain, may permit separation of different conformers.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Certain compounds of the present invention may exist in more than one crystal form (generally referred to as "polymorphs"). Polymorphs may be prepared by crystallization under various conditions, for example, using different solvents or different solvent mixtures for recrystallization; crystallization at different temperatures; and/or various modes of cooling, ranging from very fast to very slow cooling during crystallization. Polymorphs may also be obtained by heating or melting the compound of the present invention followed by gradual or fast cooling. The presence of polymorphs may be determined by solid probe NMR spectroscopy, IR spectroscopy, differential scanning calorimetry, powder X-ray diffraction or such other techniques.

Compounds of the present invention are useful for treating diseases, conditions and/or disorders modulated by the activation of the glucokinase enzyme; therefore, another embodiment of the present invention is a pharmaceutical composition comprising a therapeutically effective amount of a compound of the present invention and a pharmaceutically acceptable excipient, diluent or carrier. The compounds of the present invention (including the compositions and processes used therein) may also be used in the manufacture of a medicament for the therapeutic applications described herein.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical compositions also include solvates and hydrates of the compounds of Formula (I). The term "solvate" refers to a molecular complex of a compound represented by Formula (I) (including pharmaceutically acceptable salts thereof) with one or more solvent molecules. Such solvent molecules are those commonly used in the pharmaceutical art, which are known to be innocuous to the recipient, e.g., water, ethanol, ethylene glycol, and the like, The term "hydrate" refers to the complex where the solvent molecule is water. The solvates and/or hydrates preferably exist in crystalline form. Other solvents may be used as intermediate solvates in the preparation of more desirable solvates, such as methanol, methyl t-butyl ether, ethyl acetate, methyl acetate, (S)-propylene glycol, (R)-propylene glycol, 1,4-butyne-diol, and the like.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by the activation of the glucokinase enzyme in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders that benefit from the activation of glucokinase which include: eating disorders (e.g., binge eating disorder, anorexia, bulimia, weight loss or control and obesity), prevention of obesity and insulin resistance by glucokinase expression in skeletal muscle of transgenic mice (Otaegui, P. J., et. al., *The FASEB Journal*, 17; 2097-2099, (2003)); and Type II diabetes, insulin resistance syndrome, insulin resistance, and hyperglycemia (Poitout, V., et. al., "An integrated view of β-cell dysfunction in type-II diabetes", *Annul. Rev. Medicine*, 47; 69-83, (1996)).

One aspect of the present invention is the treatment of obesity, and obesity-related disorders (e.g., overweight, weight gain, or weight maintenance).

Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 kg/m², and obesity is typically defined as a BMI of 30 kg/m². See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

Another aspect of the present invention is for the treatment or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, and diabetic complications (such as atherosclerosis, coronary heart disease, stroke, peripheral vascular disease, nephropathy, hypertension, neuropathy, and retinopathy).

Yet another aspect of the present invention is the treatment of diabetes- or obesity-related co-morbidities, such as metabolic syndrome. Metabolic syndrome includes diseases, conditions or disorders such as dyslipidemia, hypertension, insulin resistance, diabetes (e.g., Type 2 diabetes), weight gain, coronary artery disease and heart failure. For more detailed information on Metabolic Syndrome, see, e.g., Zimmet, P. Z., et al., "The Metabolic Syndrome: Perhaps an Etiologic Mystery but Far From a Myth—Where Does the International Diabetes Federation Stand?," *Diabetes & Endocrinology*, 7(2), (2005); and Alberti, K. G., et al., "The Metabolic Syndrome—A New Worldwide Definition," *Lancet*, 366, 1059-62 (2005). Preferably, administration of the compounds of the present invention provides a statistically significant (p<0.05) reduction in at least one cardiovascular disease risk factor, such as lowering of plasma leptin, C-reactive protein (CRP) and/or cholesterol, as compared to a vehicle control containing no drug. The administration of compounds of the present invention may also provide a statistically significant (p<0.05) reduction in glucose serum levels.

In yet another aspect of the present invention, the condition treated is impaired glucose tolerance, hyperglycemia, diabetic complications such as sugar cataracts, diabetic neuropathy, diabetic nephropathy, diabetic retinopathy and diabetic cardiomyopathy, anorexia nervosa, bulimia, cachexia, hyperuricemia, hyperinsulinemia, hypercholesterolemia, hyperlipidemia, dyslipidemia, mixed dyslipidemia, hypertriglyceridemia, nonalcoholic fatty liver disease, atherosclerosis, arteriosclerosis, acute heart failure, congestive heart failure, coronary artery disease, cardiomyopathy, myocardial infarction, angina pectoris, hypertension, hypotension, stroke, ischemia, ischemic reperfusion injury, aneurysm, restenosis, vascular stenosis, solid tumors, skin cancer, melanoma, lymphoma, breast cancer, lung cancer, colorectal cancer, stomach cancer, esophageal cancer, pancreatic cancer, prostate cancer, kidney cancer, liver cancer, bladder cancer, cervical cancer, uterine cancer, testicular cancer and ovarian cancer.

The present invention also relates to therapeutic methods for treating the above described conditions in a mammal, including a human, wherein a compound of formula (I) of this invention is administered as part of an appropriate dosage regimen designed to obtain the benefits of the therapy. The appropriate dosage regimen, the amount of each dose administered and the intervals between doses of the compound will depend upon the compound of formula (I) of this invention being used, the type of pharmaceutical compositions being used, the characteristics of the subject being treated and the severity of the conditions.

In general, an effective dosage for the compounds of the present invention is in the range of 0.01 mg/kg/day to 30 mg/kg/day, preferably 0.01 mg/kg/day to 5 mg/kg/day of active compound in single or divided doses. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. Practitioners will appreciate that "kg" refers to the weight of the patient measured in kilograms.

The compounds or compositions of this invention may be administered in single (e.g., once daily) or multiple doses or via constant infusion. The compounds of this invention may also be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents.

The compounds or compositions of the present invention may be administered to a subject in need of treatment by a variety of conventional routes of administration, including orally and parenterally, (e.g., intravenously, subcutaneously or intramedullary). Further, the pharmaceutical compositions of this invention may be administered intranasally, as a suppository, or using a "flash" formulation, i.e., allowing the medication to dissolve in the mouth without the need to use water.

It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable anti-diabetic agents include an acetyl-CoA carboxylase-2 (ACC-2) inhibitor, a diacylglycerol O-acyltransferase 1 (DGAT-1) inhibitor, a phosphodiesterase (PDE)-10 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., *Drug Discovery Today*, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (JNK) inhibitor, insulin, an insulin mimetic, a glycogen phosphorylase inhibitor, and a VPAC2 receptor agonist. Preferred anti-diabetic agents are metformin and DPP-IV inhibitors (e.g., sitagliptin, vildagliptin, alogliptin and saxagliptin).

Suitable anti-obesity agents include 11β-hydroxy steroid dehydrogenase-1 (11β-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, $β_3$ adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), $PYY_{3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, and the like.

Preferred anti-obesity agents for use in the combination aspects of the present invention include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818,658), lipase inhibitor (e.g., Cetilistat), $PYY_{3-36}$ (as used herein "$PYY_{3-36}$" includes analogs, such as peglated $PYY_{3-36}$ e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, liraglutide, bromocriptine, orlistat, exenatide (Byetta®), AOD-9604 (CAS No. 221231-10-3) and sibutramine. Preferably, compounds of the present invention and combination therapies are administered in conjunction with exercise and a sensible diet.

All of the above recited U.S. patents and publications are incorporated herein by reference.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England). The following materials are available from the corresponding sources:

5-Methyl-2-furaldehyde—Sigma-Aldrich (Milwaukee, Wis.);

5-Methyl-2-aminopyrazine—Princeton Bimolecular Research, Inc (Monmouth Junction, N.J.);

5-Methoxypyrazin-2-amine—Anichem (Monmouth Junction, N.J.);

5-Chloropyrazine-2-carboxylic acid—Ark Pharma, Inc (Libertyville, Ill.);

1-Methyl-1H-pyrazol-3-yl amine—Matrix Scientific (Columbia, S.C.);

5-Bromo-pyrimidine-2-carboxylic acid—Ark Pharma, Inc (Libertyville, Ill.)

General Experimental Procedures

NMR spectra were recorded on a Varian Unity™ 400 (available from Varian Inc., Palo Alto, Calif.) at room temperature at 400 MHz for proton. Chemical shifts are expressed in parts per million (δ) relative to residual solvent as an internal reference. The peak shapes are denoted as follows: s, singlet; d, doublet; dd, doublet of doublet; t, triplet; q, quartet; m, multiplet; bs, broad singlet; 2s, two singlets. Atmospheric pressure chemical ionization mass spectra (APCI) were obtained on a Fisons™ Platform II Spectrometer (carrier gas: acetonitrile: available from Micromass Ltd, Manchester, UK). Chemical ionization mass spectra (CI) were obtained on a Hewlett-Packard™ 5989 instrument (ammonia ionization, PBMS: available from Hewlett-Packard Company, Palo Alto, Calif.). Electrospray ionization mass spectra (ES) were obtained on a Waters™ ZMD instrument (carrier gas: acetonitrile: available from Waters Corp., Milford, Mass.). High resolution mass spectra (HRMS) were obtained on an Agilent™ Model 6210 using time of flight method. Where the intensity of chlorine or bromine-containing ions are described, the expected intensity ratio was observed (approximately 3:1 for $^{35}Cl/^{37}Cl$-containing ions and 1:1 for $^{79}Br/^{81}Br$-containing ions) and the intensity of only the lower mass ion is given. In some cases only representative $^1H$ NMR peaks are given. Optical rotations were determined on a PerkinElmer™ 241 polarimeter (available from PerkinElmer Inc., Wellesley, Mass.) using the sodium D line (γ=589 nm) at the indicated temperature and are reported as follows $[α]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Flash 40 Biotage™ columns (ISC, Inc., Shelton, Conn.) or Biotage™ SNAP cartridge KPsil or Redisep Rf silica (from Teledyne™ Isco™) under low nitrogen pressure.

Preparations of Starting Materials and Key Intermediates

Preparation of Intermediate (E)-3-(ethoxycarbonyl)-4-(5-methylfuran-2-yl)but-3-enoic acid (I-1a)

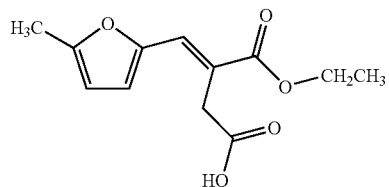

(I-1a)

To a vigorously stirred solution of 5-methyl-2-furaldehyde (264 mL, 2650 mmol) and diethyl succinate (840 mL, 5050 mmol) in ethanol (1.820 L) at room temperature was added sodium ethoxide (0.93 L of a 21 weight % solution in ethanol) in one portion. The reaction mixture was then heated at reflux for 13 hours. After cooling to room temperature, the mixture was concentrated in vacuo (all batches were combined at this point). The resulting residue was partitioned between ethyl acetate (1 L) and hydrochloric acid (1 L of a 2M aqueous solution). After separation, the aqueous layer was extracted with ethyl acetate (2×1 L). The combined organic extracts were then extracted with sodium hydrogen carbonate (2×1 L of a saturated aqueous solution). These aqueous extracts were combined and adjusted to pH 2 with hydrochloric acid (2M aqueous solution) then extracted with ethyl acetate (2×1 L). These organic extracts were combined and concentrated in vacuo to give desired (E)-3-(ethoxycarbonyl)-4-(5-methylfuran-2-yl)but-3-enoic acid (I-1a: 34.34 g, 5%). The original organic extract was extracted with sodium hydroxide (2 L of a 2M aqueous solution). This aqueous extract was adjusted to pH 2 with hydrochloric acid (2M aqueous solution) then extracted with ethyl acetate (2×1 L). These organic extracts were combined and concentrated in vacuo to give additional desired materials (395.2 gram, 63%) as red liquid.

$^1$H NMR (CDCl$_3$, 300 MHz) δ ppm 7.48 (s, 1H), 6.57 (d, 1H), 6.09 (d, 1H), 4.24 (q, 2H), 3.87 (s, 2H), 2.32 (s, 3H), 1.31 (t, 3H).

Preparation of Intermediate ethyl 4-acetoxy-2-methylbenzofuran-6-carboxylate (I-1b)

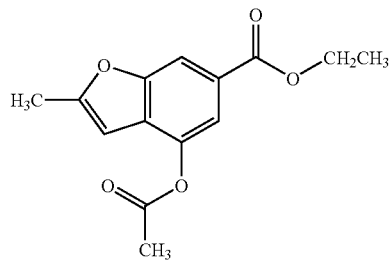

(I-1b)

To a vigorously stirred solution of (E)-3-(ethoxycarbonyl)-4-(5-methylfuran-2-yl)but-3-enoic acid (I-1a: 326.6 g, 1.371 mol) in acetic anhydride (1.77 L, 18.72 mol) at room temperature was added sodium acetate (193 g, 2350 mmol) in one portion. The reaction mixture was then heated at reflux for 2.5 hours. After cooling to room temperature, the mixture was concentrated in vacuo (all batches were combined at this point). The resulting residue was suspended in dichloromethane (1.5 L) and filtered, washing the solids with dichloromethane (3×500 mL). The combined filtrate and washings were then washed with sodium hydrogencarbonate (2×1 L of a saturated aqueous solution) and brine (2 L), then concentrated in vacuo to give desired ethyl 4-acetoxy-2-methylbenzofuran-6-carboxylate (I-1b: 549.03 g, quantitative). $^1$H NMR (CDCl$_3$, 300 MHz) δ ppm 8.00-7.99 (m, 1H), 7.64 (d, 1H), 6.32-6.32 (m, 1H), 4.38 (q, 2H), 2.47 (d, 3H), 2.37 (s, 3H), 1.39 (t, 3H).

Preparation of Intermediate ethyl 4-hydroxy-2-methylbenzofuran-6-carboxylate (I-1c)

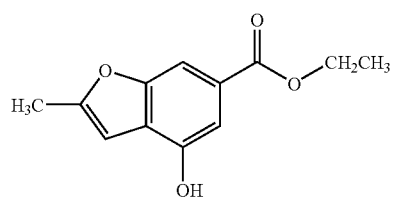

(I-1c)

To a stirred solution of ethyl 4-acetoxy-2-methylbenzofuran-6-carboxylate (I-1b: 549.03 g, 1.37 mol) in ethanol (4.00 L) at room temperature was added potassium carbonate (266 g, 1.92 mol) in one portion. The reaction mixture was then heated at 60° C. for 3 hours. Potassium carbonate (100 g, 0.720 mol) was then added in one portion and the reaction mixture was heated at 60° C. for a further 3 hours. After cooling to room temperature the mixture was diluted with dichloromethane (2 L) and the suspension filtered, washing the solids with dichloromethane (2×1 L) (all batches were combined at this point). The combined filtrate and washings were then washed with citric acid (2.5 L of a 1 M aqueous solution), then concentrated in vacuo and the resulting residue purified by dry flash chromatography (hexane then 2:1 hexane:ethyl acetate). All fractions containing the desired product were combined and concentrated in vacuo. The resulting residue, which solidified on standing, was slurried with cold toluene and filtered. The solids were then stirred with hot toluene and decolourising charcoal for 1 hour, followed by filtration of the hot mixture through a pad of celite. The filtrate was allowed to cool and the resulting precipitate isolated by filtration to give desired ethyl 4-hydroxy-2-methylbenzofuran-6-carboxylate (I-1c: 360 g, 90%) as orange powder. $^1$H NMR (CDCl$_3$, 300 MHz) δ ppm 7.73-7.73 (m, 1H), 7.45 (d, 1H), 6.51-6.50 (m, 1H), 5.85 (s, 1H), 4.39 (q, 2H), 2.48 (d, 3H), 1.40 (t, 3H). LCMS (liquid chromatography mass spectrometry): m/z 221.06 (96.39% purity).

Preparation of Starting Material 5-chloro-N,N-dimethylpyrazine-2-carboxamide (SM-1)

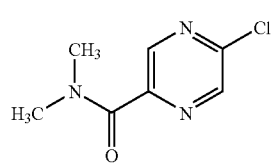

(SM-1)

5-chloropyrazine-2-carboxylic acid (1.00 gram, 6.31 mmol) in dichloromethane (30 ml) was treated with catalytic amount of dimethylformamide, followed by (COCl)₂ (0.85 ml, 9.46 mmol). The resulting mixture was stirred over night. The reaction was concentrated in vacuo, and dried under vacuum to give desired 5-chloropyrazine-2-carbonyl chloride as solid (1.05 g, 100%).

5-chloropyrazine-2-carbonyl chloride (2.13 gram, 12.05 mmol) and dimethylamine HCl salt (1.06 gram, 12.7 mmol) were suspended in dichloromethane (50 mL) with stirring. Triethylamine (5.04 mL, 36.2 mmol) in dichloromethane (25 mL) was added dropwise at 0° C. to the reaction mixture. The combined solution was warmed up to ambient temperature and stirred for 4 hours. The compound was diluted with dichloromethane, washed with 1N HCl, water, brine, dried (Na₂SO₄), filtered and concentrated. The crude product was purified by column chromatography (silica gel, gradient of 30 to 80% ethyl acetate in heptane) to provide desired 5-chloro-N,N-dimethylpyrazine-2-carboxamide (SM-1: 2.24 g, 85%).
¹H NMR (400 MHz, CHLOROFORM-d) δ ppm 8.74 (d, J=1.37 Hz, 1H) 8.53 (d, J=1.37 Hz, 1H) 3.15 (s, 3H) 3.12 (s, 3H)

Preparation of Intermediate ethyl 4-(5-(dimethylcarbamoyl)pyrazin-2-yloxy)-2-methylbenzofuran-6-carboxylate (I-1d)

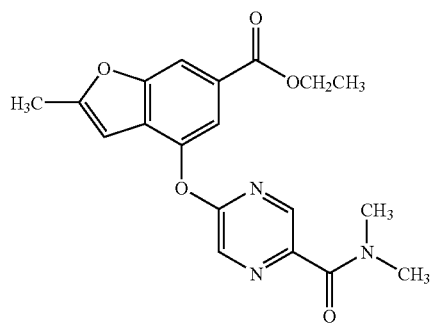

(I-1d)

The flask was charged with ethyl 4-hydroxy-2-methylbenzofuran-6-carboxylate (I-1c: 6.07 g, 27.6 mmol), 5-chloro-N,N-dimethylpyrazine-2-carboxamide (SM-1: 5.06 g, 27.3 mmol), cesium carbonate (9.78 g, 30 mmol). The solids were dissolved in dimethylformamide (60 mL). The reaction was heated to 90° C. for 3 hours. After the reaction was cooled down to ambient temperature, dimethylformamide was removed in vacuo. The crude reaction mixture was partitioned between ethyl acetate (100 ml) and water (30 mL). The aqueous layer was extracted with ethyl acetate (50 mL). The combined organic layer was washed with water, brine, dried over sodium sulfate, and concentrated. The crude product was purified by column chromatography (silica gel, 30 to 80% gradient of ethyl acetate in heptane) to give desired ethyl 4-(5-(dimethylcarbamoyl)pyrazin-2-yloxy)-2-methylbenzofuran-6-carboxylate (I-1d) as a light brown solid (8.3 g, 95%).

¹H NMR (400 MHz, CHLOROFORM-d) δ ppm 8.48 (d, J=1.17 Hz, 1H) 8.41 (d, J=0.98 Hz, 1H) 8.04 (t, J=1.07 Hz, 1H) 7.71 (d, J=1.17 Hz, 1H) 6.16-6.21 (m, 1H) 4.38 (q, J=7.22 Hz, 2H) 3.17 (s, 3H) 3.14 (s, 3H) 2.45 (d, J=1.17 Hz, 3H) 1.38 (t, J=7.12 Hz, 3H). MS (M+1): 370.1

Preparation of SM-2
5-bromo-N,N-dimethylpyrimidine-2-carboxamide (SM-2)

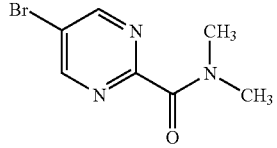

(SM-2)

Oxalyl chloride (47.4 g, 369 mmol) was added to a suspension of 5-Bromo-pyrimidine-2-carboxylic acid (50 g, 250 mmol) in dichloromethane (821 ml) at room temperature followed by 1-2 drop of dimethylformamide. The reaction mixture was stirred under nitrogen for 2 hours LCMS in methanol indicated the presence of the methyl ester and some acid. Dimethylformamide (0.2 ml) was added to the reaction mixture. The acid dissolved after 30 minutes. LCMS showed corresponding methyl ester and no starting material peak was observed. The solvent was removed and dried in vacuo to afford the crude 5-Bromo-pyrimidine-2-carbonyl chloride (55 g, 100%).

The 5-Bromo-pyrimidine-2-carbonyl chloride (55 g, 250 mmol) was dissolved in tetrahydrofuran (828 ml) and dimethyl-amine (2M solution in tetrahydrofuran) (373 ml, 745 mmol) was added portionwise at room temperature. The reaction was stirred at room temperature under nitrogen for 16 hours, after which time, LCMS indicated completion. The mixture was diluted with ethyl acetate (500 ml) and washed with H₂O (500 ml). The water layer was further extracted with CH₂Cl₂ (5×500 ml), all organics combined, and dried over magnesium sulfate. The filtrate was concentrated in vacuo and then suspended in methyl-t-butylether (650 ml). The solution was then heated to reflux. The hot solution was allowed to cool overnight to afford pink crystals. The crystals were filtered and washed with cold methyl-t-butylether (100 ml) the solid was dried in a vacuum oven at 55° C. for 12 hours to afford the title compound 5-bromo-N,N-dimethylpyrimidine-2-carboxamide (SM-2: 44 g, 77%) as a pink solid.
¹H NMR (400 MHz, CHLOROFORM-d) δ ppm 2.94 (s, 3H) 3.13 (s, 3H) 8.85 (s, 2H) m/z (M+1)=232.

Preparation of Intermediate Ethyl 4-(2-(dimethylcarbamoyl)pyrimidin-5-yloxy)-2-methylbenzofuran-6-carboxylate (I-2a)

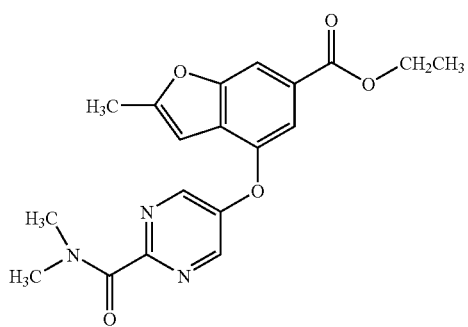

(I-2a)

A mixture of Cs₂CO₃ (62.1 g, 191 mmol), 5-bromo-N,N-dimethylpyrimidine-2-carboxamide (SM-2: 24 g, 104 mmol) and ethyl 4-hydroxy-2-methylbenzofuran-6-carboxylate (I-1c: 20 g, 91 mmol); 1,10-phenanthroline (1.64 g, 9.07 mmol) and copper iodide (864 mg, 4.54 mmol) in dimethylformamide (200 ml) was purged with $N_2$ gas and then heated to 90° C. using a mechanical stirrer. The heterogeneous reaction mixture was stirred at this temperature for 18 hours. HPLC indicated near completion. The reaction mixture was cooled to 35° C. and diluted with ethyl acetate (300 ml). The mixture was filtered to remove any cesium carbonate. The filtrate was then partitioned between water (500 ml) and ethyl acetate (500 ml); however, no separation was observed. Concentrated HCL (20 ml) was added to the mixture. When the aqueous phase was about pH1, the phases separated. The organics were separated and the aqueous layer reextracted with ethyl acetate (2×500 ml). All organics were combined and back extracted with water (200 ml) and brine (500 ml). The organics were separated and treated with activated charcoal (10 g) and magnesium sulfate. The mixture was allowed to stir for 10 minutes and then filtered through a plug of celite to afford a crude yellow solution. The filter cake was washed with ethyl acetate (100 mL). The organics were concentrated in vacuo to afford a crude solid this was dried under high vacuum for 4 days. The dry crude solid was triturated using methanol (80 mL). The solids were dispersed into a fine light orange crystalline powder with a red liquor. The solids were isolated by filtration and rinsed with methanol (20 mL). The solid was dried in the vacuum oven at 55° C. for 12 hours to afford ethyl 4-(2-(dimethylcarbamoyl)pyrimidin-5-yloxy)-2-methylbenzofuran-6-carboxylate (I-2a) as a yellow solid (18.2 g, 54%)

$^1$H NMR (400 MHz, CHLOROFORM-d) δ ppm 1.41 (t, J=7.12 Hz, 3H) 2.50 (d, J=0.98 Hz, 3H) 3.00 (s, 3H) 3.17 (s, 3H) 4.41 (d, J=7.22 Hz, 2H) 6.29 (s, 1H) 7.62 (d, J=1.17 Hz, 1H) 8.06 (s, 1H) 8.50 (s, 2H). m/z (M+1)=370.5

Preparation of Starting Material
5-bromo-N-ethyl-N-methylpyrimidine-2-carboxamide
(SM-3)

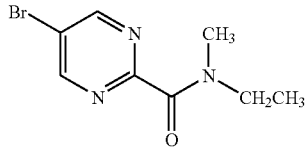

(SM-3)

Oxalyl chloride (1.45 g, 11.1 mmol) was added to a suspension of 5-Bromo-pyrimidine-2-carboxylic acid (1.5 g, 7.4 mmol) in dichloromethane (50 ml) at room temperature followed by 1-2 drop of dimethylformamide. The reaction mixture was stirred under nitrogen for 2 hours LCMS in methanol indicated the presence of the methyl ester and some acid. Dimethylformamide (0.2 ml) was added to the reaction mixture and all of the acid dissolved after 30 minutes. LCMS showed corresponding methyl ester and no starting material peak was observed. The solvent was removed and dried in vacuo to afford the crude 5-Bromo-pyrimidine-2-carbonyl chloride (1.6 g).

5-Bromo-pyrimidine-2-carbonyl chloride (1600 mg, 7.225 mmol) was dissolved in dichloromethane (25 ml) and triethylamine (4.03 ml, 28.9 mmol) was added followed by ethylmethyl-amine (0.68 mL, 7.92 mmol). The reaction was stirred at room temperature under nitrogen for 16 ours, after which time, LCMS indicated completion. The mixture was diluted with dichloromethane (50 ml) and washed with water (50 ml) followed by 10% citric acid (50 ml) and brine (50 ml). The organic layer was separated and dried over $MgSO_4$, the residue was filtered and the solvent was removed in vacuo to afford the title compound 5-bromo-N-ethyl-N-methylpyrimidine-2-carboxamide (SM-3): (1.4 g, 79.4%) as a brown oil.

$^1$H NMR (400 MHz, CHLOROFORM-d) δ ppm 1.08-1.31 (m, 3H) 2.99 (d, J=79.05 Hz, 3H) 3.19 (q, J=7.22 Hz, 1H) 3.59 (q, J=7.22 Hz, 1H) 8.84 (d, J=3.12 Hz, 2H)

Preparation of Intermediate Ethyl 4-(2-(ethyl(methyl)carbamoyl)pyrimidin-5-yloxy)-2-methylbenzofuran-6-carboxylate (I-5a)

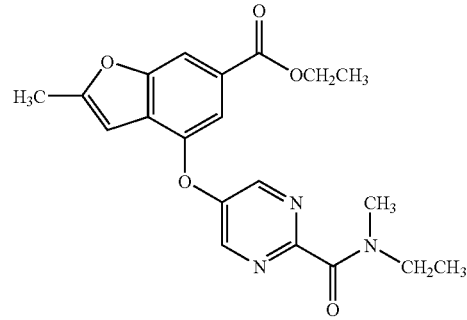

(I-5a)

The flask was charged with 5-bromo-N-ethyl-N-methylpyrimidine-2-carboxamide (SM-3: 615 mg, 2.5 mmol), ethyl 4-hydroxy-2-methylbenzofuran-6-carboxylate (I-1c: 378 mg, 1.7 mmol), $Cs_2CO_3$ (1.15 g, 3.5 mmol), 1,10-phenanthroline (30.3 mg, 0.17 mmol), copper iodide (16 mg, 0.08 mmol) and dimethylformamide (17 mL). The reaction mixture was degassed with $N_2$ for 5 minutes and then heated to 90° C. for 16 hours under a $N_2$ atmosphere. The reaction mixture was diluted with ethylacetate (250 mL), washed with water (3×100 mL), dried ($MgSO_4$) and concentrated. The crude material was purified by a biotage 50 g silica gel column (20%-100% EtOAc in Hep) to afford the title compound ethyl 4-(2-(ethyl(methyl)carbamoyl)pyrimidin-5-yloxy)-2-methylbenzofuran-6-carboxylate (I-5a: 180 mg, 28%) as a yellow solid.

$^1$H NMR (400 MHz, CHLOROFORM-d) δ ppm 1.07-1.26 (m, 3H) 1.34 (t, J=7.12 Hz, 3H) 2.42 (d, J=0.98 Hz, 3H) 2.97 (d, J=65.77 Hz, 3H) 3.14-3.66 (m, 2H) 4.33 (q, J=7.22 Hz, 2H) 6.14-6.32 (m, 1H) 7.54 (dd, J=3.32, 1.17 Hz, 1H) 7.92-8.04 (m, 1H) 8.43 (d, J=4.10 Hz, 2H). MS (M+1)=384.3

Preparation of Starting material
5-chloro-N-ethyl-N-methylpyrazine-2-carboxamide
(SM-4)

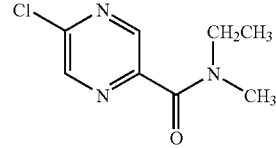

(SM-4)

The title compound (I-7a) was prepared by a method analogous to that described for the preparation of SM-1 using 5-chloropyrazine-2-carboxylic acid (2 g, 12.62 mmol) and ethyl-methyl-amine (0.846 g, 13.9 mmol) to afford the title compound 5-chloro-N-ethyl-N-methylpyrazine-2-carboxamide (SM-4: 2.05 g, 81%) as a clear oil ¹H NMR (400 MHz, CHLOROFORM-d) δ ppm 8.72 (dd, J=7.41, 1.37 Hz, 1H), 8.53 (d, J=1.56 Hz, 1H), 3.60 (q, J=7.22 Hz, 1H), 3.42 (q, J=7.02 Hz, 1H), 3.09 (d, J=10.73 Hz, 3H), 1.17-1.31 (m, 3H).

Preparation of Intermediate ethyl 4-(5-(ethyl(methyl)carbamoyl)pyrazin-2-yloxy)-2-methylbenzofuran-6-carboxylate (I-7a)

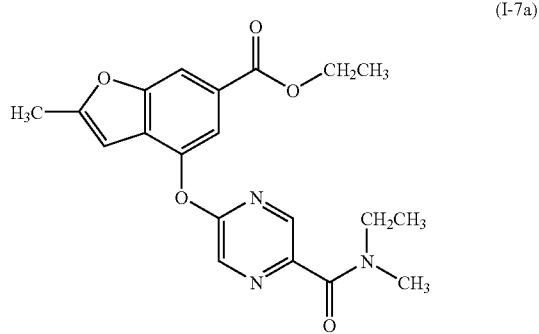

(I-7a)

Ethyl 4-hydroxy-2-methylbenzofuran-6-carboxylate (I-1c: 2.25 g, 10.22 mmol), potassium carbonate (2.1 g, 15.3 mmol), 5-chloro-N-ethyl-N-methylpyrazine-2-carboxamide (SM-4: 2.04 g, 10.2 mmol) were mixed in acetonitrile (30 ml). The mixture was heated at 100° C. over night, after which time, the reaction mixture was diluted with ethylacetate (50 ml) and filtered. The organic layer was concentrated and purified by column chromatography on silica gel eluting with ethylacetate in heptanes 20-100% to afford ethyl 4-(5-(ethyl(methyl)carbamoyl)pyrazin-2-yloxy)-2-methylbenzofuran-6-carboxylate (I-7a: (3.9 g, 99.5%) as a gum.

¹H NMR (400 MHz, CHLOROFORM-d) δ ppm 8.45 (dd, J=7.43, 1.17 Hz, 1H), 8.40 (s, 1H), 8.04 (t, J=1.07 Hz, 1H), 7.71 (d, J=0.98 Hz, 1H), 6.18 (d, J=0.98 Hz, 1H), 4.38 (q, J=7.04 Hz, 2H), 3.60 (q, J=7.23 Hz, 1H), 3.48 (q, J=6.91 Hz, 1H), 3.11 (d, J=10.36 Hz, 3H), 1.38 (t, J=7.13 Hz, 3H), 1.20-1.28 (m, 3H).

Example 1

Preparation of N,N-dimethyl-5-(2-methyl-6-((5-methylpyrazin-2-yl)carbamoyl-benzofuran-4-yloxy)pyrazine-2-carboxamide (I)

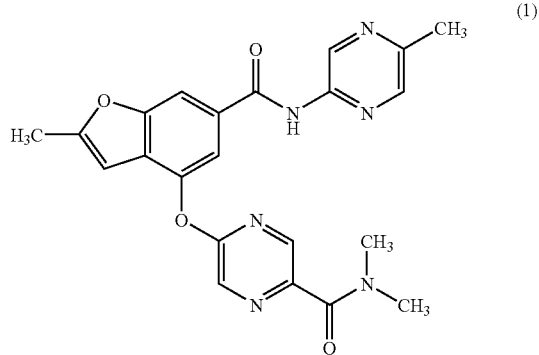

(1)

5-methyl-2-aminopyrazine (6.8 g, 63 mmol) was taken up in 70 mL of dimethylether and cooled to 0° C. Dimethylaluminium chloride (131 mmol, 1 M in hexane) was added dropwise. The resulting mixture was warmed up to ambient temperature and stirred for 30 min. Ethyl 4-(5-(dimethylcarbamoyl)pyrazin-2-yloxy)-2-methylbenzofuran-6-carboxylate (I-1d: 10.1 g, 27.3 mmol) in dimethylether (70 mL) was then added to the activated amine solution via canula. The combined solution was heated to reflux overnight. The reaction was cooled on ice and slowly quenched by the dropwise addition of aqueous Rochelle's salt (concentrated, 100 mL). The mixture was stirred for 20 minutes. The mixture was separated. Organic layer was washed with aqueous Rochelle's salt (30 ml), 1N HCl (30 ml), brine (30 ml), dried over sodium sulfate, and concentrated in vacuo. The crude product was purified by column chromatography (silica gel, gradient of ethyl acetate from 50-100% in heptane) to give desired N,N-dimethyl-5-(2-methyl-6-((5-methylpyrazin-2-yl)carbamoyl)benzofuran-4-yloxy)pyrazine-2-carboxamide (1: 8.5 gram 72%).

¹H NMR (400 MHz, CHLOROFORM-d) δ ppm 9.57 (d, J=1.37 Hz, 1H) 8.49 (d, J=1.37 Hz, 1H) 8.45 (d, J=1.37 Hz, 1H) 8.42 (s, 1H) 8.14 (dd, J=1.56, 0.59 Hz, 1H) 7.91-7.94 (m, 1H) 7.62 (d, J=1.37 Hz, 1H) 6.22 (t, J=0.98 Hz, 1H) 3.18 (s, 3H) 3.15 (s, 3H) 2.55 (s, 3H) 2.48 (d, J=1.17 Hz, 3H)
MS (M+1): 433.1.

Example 2

Preparation of N,N-dimethyl-5-(2-methyl-6-((5-methylpyrazin-2-yl)carbamoyl)-benzofuran-4-yloxy)pyrimidine-2-carboxamide (2)

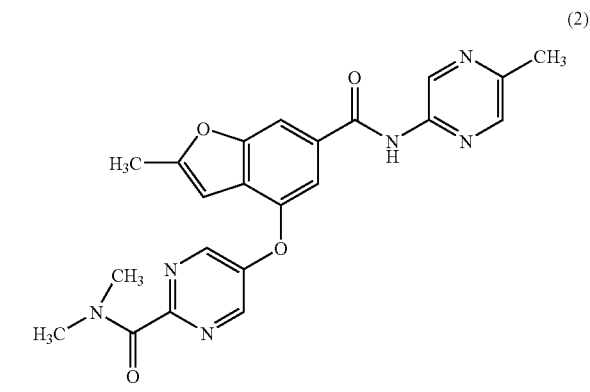

(2)

To a solution of the 5-methyl-2-aminopyrazine (38.9 g, 356 mmol) in dimethylether (315 mL) in a 3-neck flask equipped with overhead stirring and a condenser at 0° C. was added Me₂AlCl (1M solution in hexanes) (715 mL). The mixture was warmed at room temperature and stirred for 1.5 hours. In a separate flask, ethyl 4-(2-(dimethylcarbamoyl)pyrimidin-5-yloxy)-2-methylbenzofuran-6-carboxylate (1-2a: 52.6 g, 142.5 mmol) was dissolved in dimethylether (210 mL). This mixture was then added to the complexed amine. A gum precipitated upon scratching the flask and dissipated into a solid. The resultant reaction was refluxed for 3.5 hours HPLC indicated 93% complete. Five liters of Rochelles salt made up in water and 2 liters of 2-methyltetrahydrofuran was added to the mixture. The reaction mixture was then poured into the biphasic system. The mixture was allowed to stir with overhead stirring for 14 hours, after which time, a yellow solid precipitated. The solid was collected through filtration. The solid retained was washed with 2-methyltetrahydrofuran. The resultant solid was dried in vacuo oven overnight to afford the title compound N,N-dimethyl-5-(2-methyl-6-((5-methylpyrazin-2-yl)carbamoyl)benzofuran-4-yloxy)pyrimidine-2-carboxamide (2): (49.98 g, 81%)

¹H NMR (400 MHz, CHLOROFORM-d) d ppm 2.49 (d, J=1.17 Hz, 3 H) 2.55 (s, 3H) 2.98 (s, 3H) 3.14 (s, 3H) 6.28 (t, J=0.98 Hz, 1H) 7.52 (d, J=1.37 Hz, 1H) 7.88-7.92 (m, 1H) 8.14 (d, J=0.78 Hz, 1H) 8.37 (s, 1H) 8.50 (s, 2H) 9.54 (d, J=1.56 Hz, 1H). m/z (M+1)=433.4, m/z (M−1)=431.5

Example 3

Preparation of 5-(6-((5-methoxypyrazin-2-yl)carbamoyl)-2-methylbenzofuran-4-yloxy)-N,N-dimethylpyrimidine-2-carboxamide (3)

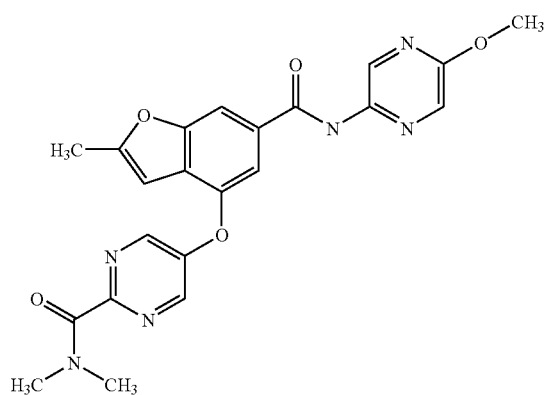

(3)

The title compound (3) was prepared by a method analogous to that described in Example 1 using 5-methoxypyrazin-2-amine and ethyl 4-(2-(dimethylcarbamoyl)-pyrimidin-5-yloxy)-2-methylbenzofuran-6-carboxylate (I-2a).

¹H NMR (400 MHz, CHLOROFORM-d) δ ppm 2.49 (s, 3H), 2.99 (s, 3H), 3.15, (s, 3H), 3.98 (s, 3H), 6.28 (s, 1H), 7.51 (s, 1H), 7.89 (s, 1H), 7.94 (s, 1H), 8.30 (s, 1H), 8.50 (s, 2H), 9.17 (s, 1H). m/z=449.1 (MH+)

Example 4

Preparation of N,N-dimethyl-5-(2-methyl-6-((1-methyl-1H-pyrazol-3-yl)-carbamoyl)benzofuran-4-yloxy)pyrimidine-2-carboxamide (4)

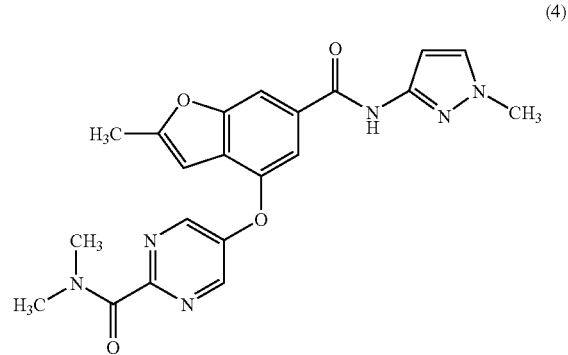

(4)

The title compound (4) was prepared by a method analogous to that described in Example 1 using 1-methyl-1H-pyrazol-3-amine and ethyl 4-(2-(dimethylcarbamoyl)pyrimidin-5-yloxy)-2-methylbenzofuran-6-carboxylate (I-2a)

¹H NMR (400 MHz, CHLOROFORM-d) δ ppm 8.55 (br. s., 2H), 8.08 (s, 1H), 7.41-7.42 (m, 1H), 7.03-7.05 (m, 1H), 6.34 (s, 1H), 3.92 (s, 3H), 3.19 (s, 3H), 3.09 (s, 3H), 2.50 (s, 3H). m/z=421.1 (MH+)

Example 5

Preparation of N-ethyl-N-methyl-5-(2-methyl-6-((5-methylpyrazin-2-yl)carbamoyl)benzofuran-4-yloxy)pyrimidine-2-carboxamide (5)

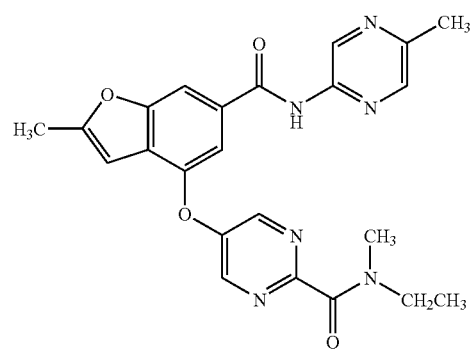

(5)

The title compound (5) was prepared by a method analogous to that described in Example 1 using ethyl 4-(2-(ethyl (methyl)carbamoyl)pyrimidin-5-yloxy)-2-methylbenzofuran-6-carboxylate (I-5a: 99 mg, 0.26 mmol), 5-methyl-2-aminopyrazine (84 mg, 0.77 mmol), dimethylaluminium chloride (1.29 mmol, 1M in hexane) and dimethylethere (4.5 mL) to afford N-ethyl-N-methyl-5-(2-methyl-6-((5-methylpyrazin-2-yl)carbamoyl)benzofuran-4-yloxy)pyrimidine-2-carboxamide (5: 70 mg, 61%) as an off white solid.

¹H NMR (400 MHz, CHLOROFORM-d) δ ppm 1.15-1.24 (m, 3H) 2.44 (s, 3H) 2.49 (s, 3H) 2.99 (d, J=58.94 Hz, 3H) 3.20-3.59 (m, 2H) 6.23 (d, J=1.17 Hz, 1H) 7.50 (dd, J=2.93, 1.17 Hz, 1H) 7.89 (d, J=1.17 Hz, 1H) 8.01 (s, 1H) 8.46 (d, J=4.10 Hz, 2H) 9.22 (d, J=3.71 Hz, 1H) 9.48 (s, 1H). MS (M+1): 447.3

Example 6

Preparation of N-ethyl-N-methyl-5-(2-methyl-6-((1-methyl-1H-pyrazol-3-yl)carbamoyl)benzofuran-4-yloxy)pyrimidine-2-carboxamide (6)

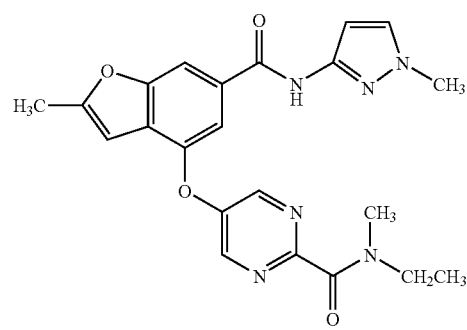

(6)

The title compound (6) was prepared by a method analogous to that described in Example 1 using ethyl 4-(2-(ethyl (methyl)carbamoyl)pyrimidin-5-yloxy)-2-methylbenzofuran-6-carboxylate (I-5a: 90 mg, 0.24 mmol), 5-methyl-2-aminopyrazine (84 mg, 0.70 mmol), dimethylaluminium chloride (1.17 mmol, 1M in hexane) and dimethylether (4.5 mL) to afford the title compound N-ethyl-N-methyl-5-(2-methyl-6-((1-methyl-1H-pyrazol-3-yl)carbamoyl)benzofuran-4-yloxy)pyrimidine-2-carboxamide (6: 49 mg, 48%).

$^1$H NMR (400 MHz, CHLOROFORM-d) δ ppm 1.12-1.26 (m, 3H) 2.43 (s, 3H) 2.99 (d, J=63.04 Hz, 3H) 3.20-3.60 (m, 2H) 3.68 (s, 3H) 6.22 (s, 1H) 6.78 (d, J=1.56 Hz, 1H) 7.18-7.30 (m, 1H) 7.47 (d, J=2.93 Hz, 1H) 7.82 (s, 1H) 8.43 (d, J=4.10 Hz, 2H) 9.18 (s, 1H). MS (M+1): 435.3

Example 7

Preparation of N-ethyl-N-methyl-5-(2-methyl-6-((5-methylpyrazin-2-yl)carbamoyl)-benzofuran-4-yloxy)pyrazine-2-carboxamide (7)

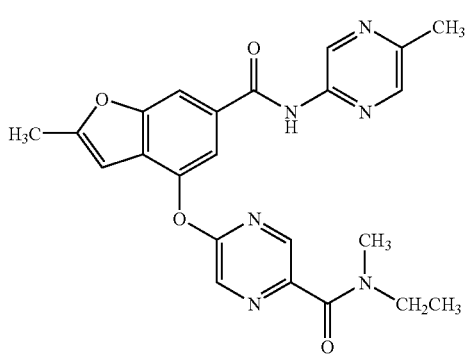

The title compound (7) was prepared by a method analogous to that described in Example 1 using ethyl 4-(5-(ethyl(methyl)carbamoyl)pyrazin-2-yloxy)-2-methylbenzofuran-6-carboxylate (I-7a: 2.5 g, 6.52 mmol); 5-methyl-2-aminopyrazine (1.42 g, 13 mmol), dimethylaluminium chloride (26.1 mmol, 1M in hexane) and dimethylether (50 mL) to afford N-ethyl-N-methyl-5-(2-methyl-6-((5-methylpyrazin-2-yl)carbamoyl)-benzofuran-4-yloxy)pyrazine-2-carboxamide (7: 2.89 g, 99%) as an off white solid.

$^1$H NMR (400 MHz, CHLOROFORM-d) δ ppm 9.56 (d, J=1.37 Hz, 1H), 8.37-8.52 (m, 2H), 8.13 (d, J=0.78 Hz, 1H), 7.93 (t, J=1.07 Hz, 1H), 7.61 (s, 1H), 6.10-6.27 (m, 1H), 3.60 (q, J=7.17 Hz, 1H), 3.40-3.53 (m, 1H), 3.12 (d, J=12.70 Hz, 3H), 2.55 (s, 3H), 2.47 (s, 3H), 1.22-1.28 (m, 3H). MS (M+1): 447.3 (M−1) 445.4

Pharmacological Testing

The practice of the instant invention for the treatment of diseases modulated by the activation of the glucokinase enzyme can be evidenced by activity in at least one of the protocols described hereinbelow. The following acronyms are used in the assay below and have the corresponding definitions. The source of supply is provided in parenthesis.

HEPES—N-[2-Hydroxyethyl]piperazine-N'-[2-ethanesulfonic acid](Sigma)
NADH—Beta-Nicotinamide adenine di-nucleotide, reduced form (Sigma)
PEP—Phosphoenolpyruvate (Sigma)
ATP—Adenosine triphosphate (Sigma)
DTT—Dithiothreitol (Sigma)
PK/LDH=Pyruvate kinase/Lactate dehydrogenase coupling enzymes (Sigma)
Glucose—(Calbiochem)
BSA—Bovine serum albumin Cohn fraction (Calbiochem)
Beta cell glucokinase (Molecular Biology)

In Vitro Assay

Full-length glucokinase (beta cell isoform) was His-tagged at N-terminus and purified by a Ni column followed by size exclusion chromatography. A 320 mL column was packed in house using Superdex75 (Amersham Pharmacia, Carlsbad, Calif.) preparation grade resin. Glucose was obtained from Calbiochem (San Diego, Calif.) and other reagents were purchased from Sigma-Aldrich (St. Louis, Mo.).

All assays were performed in a Corning 384-well plate using Spectramax PLUS spectrophotometer (Molecular Devices, Sunnyvale, Calif.) at room temperature. The final assay volume was 40 µL. The buffer conditions used in this assay were as follows: 50 mM HEPES, 5 mM glucose, 2.5 mM ATP, 3.5 mM MgCl$_2$, 0.7 mM NADH, 2 mM dithiothreitol, 1 unit/mL pyruvate kinase/lactate dehydrogenase (PK/LDH), 0.2 mM phosphoenolpyruvate, and 25 mM KCl. The buffer pH was 7.1. The test compound in dimethylsulfoxide solution was added to the buffer and mixed by a plate shaker for 7.5 minutes. The final concentration of dimethylsulfoxide introduced into the assay was 0.25%.

Glucokinase was added to the buffer mixture to initiate the reaction in the presence and absence of compound. The reaction was monitored by absorbance at 340 nm due to the depletion of NADH. The initial reaction velocity was measured by the slope of a linear time course of 0-300 seconds. The percentage of maximum activation was calculated by the following equation:

$$\% \text{ Maximum Activation} = (Va/Vo - 1) \times 100;$$

wherein each of Va and Vo is defined as the initial reaction velocity in the presence and absence of the tested compound, respectively.

To determine the EC$_{50}$ (half maximal effective concentration) and % maximum activation, compounds were serially diluted in dimethylsulfoxide by 3-fold. The glucokinase activities were measured as a function of compound concentrations. The data were fitted to the equation below to obtain the EC$_{50}$ and % max activation values:

$$Va/Vo = 1 + (\% \text{ max activation}/100)/(1 + EC_{50}/\text{compound concentration})$$

Beta Cell Glucokinase His-Tag Purification

Growth and Induction Conditions:

BL21(DE3) cells (Invitrogen Corporation, Carlsbad, Calif.) containing pBCGK (C or N H is) vector were grown at 37° C. (in 2XYT) until the OD600 was between 0.6-1.0. Expression was induced by addition of isopropylthiogalactoside to a final concentration of 0.1-0.2 mM to the cells which were then incubated overnight at 23° C. The next day, cells were harvested via centrifugation at 5000 rpm for 15 minutes at 4° C. The cell pellet was stored at −80° C. for future purification.

Purification:

A Ni-NTA (Quigan, Germantown, Md.) column (15-50 mL) was used for separation. Two buffers were prepared, 1) a lysis/nickel equilibration and wash buffer and 2) a nickel elution buffer. The lysis/equilibration/wash buffer was prepared as such: 25 mM HEPES buffer at pH 7.5, 250 mM NaCl, 20 mM imidazole, and 14 mM β-mercaptoethanol as final concentrations. The elution buffer was prepared as such: 25 mM HEPES at pH 7.5, 250 mM NaCl, 400 mM imidazole, and 14 mM β-mercaptoethanol as final concentrations. The buffers were each filtered with a 0.22 μm filter prior to use. The cell pellet (1 L culture) was resuspended in 300 mL of the lysis/equilibration buffer. The cells were then lysed (3 times) with a Microfluidics Model 110Y microfluidizer (Microfluidics Corporation, Newton, Mass.). The slurry was centrifuged with a Beckman Coulter Model LE-80K ultracentrifuge (Beckman Coulter, Fullerton, Calif.) at 40,000 rpm for 45 minutes at 4° C. The supernatant was transferred to a chilled flask. A volume of 20 μl was saved for gel analysis. A Pharmacia AKTA (GMI, Inc., Ramsey, Minn.) purification system was used for separation. The prime lines were purged with lysis/equilibration buffer. The Ni-NTA column was equilibrated with 200 mL of the lysis/equilibration buffer at a flow rate of 5 mL/minute. The supernatant was loaded over the column at 4 mL/minute and the flow-through was collected in a flask. The unbound proteins were washed with lysis/equilibration buffer at a flow rate of 5 mL/minute until the ultraviolet reaches baseline. The protein was then eluted from the column with the imidazole elution buffer via imidazole gradient 20 mM to 400 mM over 320 mL. The column was then stripped of any additional protein with 80 mL of the elution buffer. The elution fractions were each 8 mL, for a total yield of 50 samples. Fractions were analyzed by sodium dodecyl sulfate polyacrylamide (SDS-PAGE) and the fractions containing protein of interest were pooled and concentrated to 10 mL using ultrafiltration cell with a 10,000 molecular weight cut-off (MWCO) Millipore membrane (Sigma-Aldrich, St. Louis, Mo.) under nitrogen gas (60 psi). Protein was further purified by size exclusion chromatography (SEC) using a Sedex 75 evaporative light scattering detector (320 mL) (Amersham Pharmacia, Uppsala, Sweden). SEC was equilibrated with 450 mL sizing buffer containing 25 mM HEPES pH 7.0, 50 mM NaCl, and 5 mM dithiothreitol. Concentrated protein was then loaded over SEC and elution with 400 mL sizing buffer was performed overnight at 0.5 mL/minute. The elution fractions were 5 mL each. The fractions were analyzed by SDS-PAGE and protein containing fractions were pooled. Concentration was measured using Bradford Assay/BSA Standard. Purified protein was stored in small aliquots at −80° C.

The $EC_{50}$ (μM) and Maximum Activation (%) data is summarized in Table 1 below.

TABLE 1

| Example No. | IUPAC Name | Glucokinase $EC_{50}$ | Maximum Activation (%) |
|---|---|---|---|
| 1 | N,N-dimethyl-5-(2-methyl-6-((5-methylpyrazin-2-yl)carbamoyl-benzofuran-4-yloxy)pyrazine-2-carboxamide | 0.412 μM (n = 11) | 60.8% |
| 2 | N,N-dimethyl-5-(2-methyl-6-((5-methylpyrazin-2-yl)-carbamoyl)benzofuran-4-yloxy)pyrimidine-2-carboxamide | 0.555 μM (n = 7) | 54.7% |
| 3 | 5-(6-((5-methoxypyrazin-2-yl)carbamoyl)-2-methyl-benzofuran-4-yloxy)-N,N-dimethylpyrimidine-2-carboxamide | 0.462 μM (n = 6) | 69.5% |
| 4 | N,N-dimethyl-5-(2-methyl-6-((1-methyl-1H-pyrazol-3-yl)-carbamoyl)benzofuran-4-yloxy)pyrimidine-2-carboxamide | 0.629 μM (n = 1) | 63.9% |
| 5 | N-ethyl-N-methyl-5-(2-methyl-6-((5-methylpyrazin-2-yl)-carbamoyl)benzofuran-4-yloxy)pyrimidine-2-carboxamide | 0.546 μM (n = 2) | 57.6% |
| 6 | N-ethyl-N-methyl-5-(2-methyl-6-((1-methyl-1H-pyrazol-3-yl)carbamoyl)benzofuran-4-yloxy)pyrimidine-2-carboxamide | 0.382 μM (n = 3) | 54.1% |
| 7 | N-ethyl-N-methyl-5-(2-methyl-6-((5-methylpyrazin-2-yl)carbamoyl)-benzofuran-4-yloxy)pyrazine-2-carboxamide | 0.474 μM (n = 3) | 63.4% |

We claim:
1. N,N-dimethyl-5-(2-methyl-6-((5-methylpyrazin-2-yl)carbamoyl)benzofuran-4-yloxy)pyrimidine-2-carboxamide or a pharmaceutically acceptable salt thereof.

2. A compound having the structure

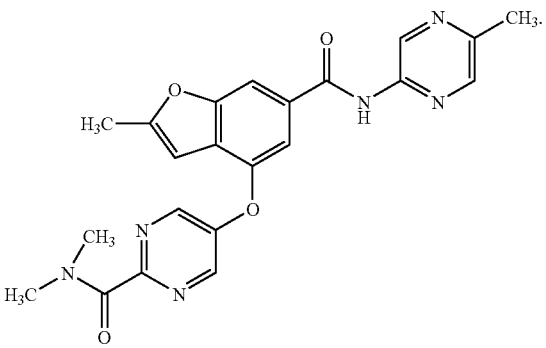 [SMILES: Cc1cnc(NC(=O)c2cc(Oc3cnc(C(=O)N(C)C)nc3)c3cc(C)oc3c2)cn1]

3. A pharmaceutical composition comprising (i) a compound of claim 1 or a pharmaceutically acceptable salt thereof; and (ii) a pharmaceutically acceptable excipient, diluent, or carrier.

4. The composition of claim 3 wherein said compound or said pharmaceutically acceptable salt thereof is present in a therapeutically effective amount.

5. A method for treating obesity and obesity-related disorders in animals comprising the step of administering to an animal in need of such treatment a therapeutically effective amount of a compound of claim 1 or a pharmaceutically acceptable salt thereof.

6. A method for treating Type II diabetes in a human comprising the step of administering to the human in need of such treatment a therapeutically effective amount of a compound of claim 1 or a pharmaceutically acceptable salt thereof.

* * * * *